US006861229B2

(12) United States Patent
Carrión et al.

(10) Patent No.: US 6,861,229 B2
(45) Date of Patent: Mar. 1, 2005

(54) METHOD OF IDENTIFYING A GENE PRODUCT

(75) Inventors: Miguel E. Carrión, New Market, MD (US); Imre Kovesdi, Rockville, MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 10/336,702

(22) Filed: Jan. 3, 2003

(65) Prior Publication Data

US 2003/0143609 A1 Jul. 31, 2003

Related U.S. Application Data

(63) Continuation of application No. PCT/US01/21445, filed on Jul. 6, 2001.
(60) Provisional application No. 60/272,943, filed on Mar. 2, 2001, and provisional application No. 60/216,174, filed on Jul. 6, 2000.

(51) Int. Cl.[7] .................. G01N 33/53; C12N 15/63; C12N 15/70; C11N 15/861
(52) U.S. Cl. .................. 435/7.1; 435/456; 435/471; 435/455
(58) Field of Search .................. 435/7.1, 455, 456, 435/471, 6, 320.1

(56) References Cited

U.S. PATENT DOCUMENTS

| | | |
|---|---|---|
| 5,174,962 A | 12/1992 | Brennan |
| 5,493,115 A | 2/1996 | Deinzer et al. |
| 5,538,897 A * | 7/1996 | Yates et al. .................. 436/89 |
| 5,605,798 A | 2/1997 | Köster |
| 5,719,060 A | 2/1998 | Hutchens et al. |
| 5,723,031 A | 3/1998 | Dürr et al. |
| 5,939,250 A | 8/1999 | Short |
| 5,965,358 A | 10/1999 | Carrión et al. |
| 6,114,111 A | 9/2000 | Luo et al. |

FOREIGN PATENT DOCUMENTS

| | | |
|---|---|---|
| WO | WO 97/19110 A | 5/1997 |
| WO | WO 97/20918 A | 6/1997 |
| WO | WO 97/43301 A | 11/1997 |
| WO | WO 99/28745 A | 6/1999 |
| WO | WO 99/36516 A | 7/1999 |
| WO | WO 00/23564 A | 4/2000 |
| WO | WO 01/11087 A | 2/2001 |

OTHER PUBLICATIONS

Tanahashi et al., Biochem. Biophys. Res. Comm 255, pp. 663–667 (1999).*
Dey et al., J. Biol. Chem., vol. 273, No. 37, pp. 24095–24101 (1998).*
Zambrano et al., J. Biol. Chem., vol. 273, No. 32, pp. 20128–20133 (1998).*
Elangovan et al., J. Biol. Chem., vol. 272, No. 39 pp. 24494–24498, (1987).*
Germino et al., Proc. Natl. Acad. Sci., 90, pp. 933–937 (1993).*
Berkner, Curr. Top. Microbiol. and Immunol., 158, pp. 39–66 (1992).*
ANONYMOUS, "Probing Viruses with Mass Spec," *R & D Magazine*, p. 33 (Jun., 1998).
Blackstock et al., *Tibtech*, 17, 121–127 (1999).
Bothner et al., *J. Biol. Chem.*, 273, 673–76 (1997).
Bothner et al., *Nature Structural Biology*, 6 (2), 114–116 (1999).
Corman et al., *Biomedical and Environmental Mass Spectrometry*, 19, 646–654 (1990).
Davison et al., *Virology*, 206, 1035–1043 (1995).
Despeyroux et al., *Rapid Communications in Mass Spectrom.*, 10, 937–41 (1996).
Fenselau, *Ann. Rev. Biophys. Biophys. Chem.*, 20, 205–220 (1991).
Fetzer et al., *Protein Expression and Purification*, 5, 432–441 (1994).
Glocker et al., *Biochemistry*, 35, 14625–14633 (1996).
Gross et al., *Spectrom. Online*, (May 28, 1998).
Hillenkamp et al., *Anal. Chem.*, 63 (24), 1193A–1203A (Dec. 15, 1991).
Hillenkamp et al., *Biological Mass Spectrom., Proceedings of the Second International Symposium on Mass Spectrometry in the Health and Life Sciences*, San Francisco, CA, Aug. 27–31, 1989, 49–60 (1990).
Jurinke et al., *Genetic Analysis: Biomolecular Engineering*, 13, 67–71 (1996).
Koenigs et al., *Biochemistry*, 38, 2312–2319 (1999).
Lamond et al., *Trends in Cell Biol.*, 7, 139–142 (Apr. 1997).
Link et al., *Nat. Biotechnol.*, 17, 676–682 (Jul. 1999).
Maizel et al., *Virology*, 36, 126–136 (1968).
Mann et al., *Anal. Chem.*, 66 (24), 4390–4399 (1994).

(List continued on next page.)

Primary Examiner—Terry McKelvey
Assistant Examiner—Nancy T. Vogel
(74) Attorney, Agent, or Firm—Leydig, Voit & Mayer, Ltd.

(57) ABSTRACT

The present invention provides a method of identifying a gene product. The method comprises providing a multiplicity of cells comprising a first gene product. Preferably, the first gene product is produced in the multiplicity of cells by expressing a first exogenous nucleic acid sequence encoding the first gene product. A library of second nucleic acid sequences encoding second gene products is then introduced into the multiplicity of cells. The second nucleic acid sequences are expressed in the multiplicity of cells to produce the second gene products such that the first gene product and at least one of the second gene products contact. The method further comprises causing a complex to form between the first gene product, an affinity molecule that binds the first gene product, and at least one of the second gene products, and subsequently retrieving the complex. At least one second gene product of the complex then is identified.

18 Claims, No Drawings

OTHER PUBLICATIONS

Marmey et al., *Virology*, 253, 319–325 (1999).
McCormack et al., *Anal. Chem.*, 69, 767–776 (Feb. 1997).
Nakanishi et al., *Biological Mass Spectrometry*, 23, 230–233 (1994).
Owens et al., *Bioorg. Med. Chem.*, 6, 1547–1554 (1998).
Pepinsksy et al., *J. Virol.*, 70, 3313–18 (1996).
Roepstorff, *Curr. Opin. Biotechnol.*, 8, 6–13 (1997).
Romano et al., *Mol. Cell. Biol.*, 18 (2), 2282–2297 (1998).
Salmon et al., *Protein Expression and Purification*, 9, 203–210 (1997).
Schriemer et al., *Anal. Chem.*, 70 (8), 1569–1575 (1998).
Siuzdak et al., *Chemistry & Biology*, 3 (1), 45–48 (1996).
Siudzak, *J. Mass Spectrom.*, 33, 203–211 (1998).
Sönksen et al., *Anat. Chem.*, 70, 2731–2736 (Jul. 1998).
Streckert et al., *Intervirology*, 36, 128–133 (1993).
Summerford et al., *Nature Med.*, 5 (5), 587–588 (1999).
Taranenko et al., *Nucl. Acids Res.*, 26 (10), 2488–2490 (1998).
Tas et al., *Biomedical and Environmental Mass Spectrometry*, 18, 757–760 (1989).
Thomas et al., *Anal. Chem.*, 70 (18), 3863–3867 (1998).
Tissue, "Mass Spectrometry Ionization Methods," *Scimedia* (Nov. 3, 1996).
Uyeda et al., *The Journal of Antibiotics*, 51 (9), 823–828 (1998).
van der Greef et al., *Biomedical and Environmental Mass Spectrometry*, 16, 45–50 (1988).
Vastola et al., *Organic Mass Spectrometry*, 3, 101–104 (1969).
Yates, *Trends in Genet.*, 16 (1), 5–8 (Jan. 2000).
Yu et al., *J. Am. Soc. Mass Spectrom.*, 9, 208–215 (1998).
Crystal, *Science*, 270, 404–410 (1995).
Sewalt et al., *Mol. Cell. Biol.*, 19 (1), 777–787 (Jan. 1, 1999).

\* cited by examiner

METHOD OF IDENTIFYING A GENE PRODUCT

TECHNICAL FIELD OF THE INVENTION

This invention pertains to the use of genetic libraries to identify a gene product of interest.

BACKGROUND OF THE INVENTION

The DNA and protein sciences have made great strides over the past two decades. Researchers have accomplished the previously unthinkable by sequencing the entire genomes of several microorganisms. The genomes of several higher eukaryotes, including mammals, are nearly completely sequenced and available on a variety of databases. Potential use of the sequence information collected to date is limitless if links between genetic sequence and cell function can be established. In order to capitalize on the seemingly endless supply of sequenced genomes, researchers have developed genetic libraries that can be screened to associate a nucleic acid sequence with a protein or peptide or cellular function. In many instances, detection involves hybridizing to the unknown DNA sequence a probe specific for a desired sequence. Yet, such probes only detect sequence motifs, and peptide function cannot be accurately predicted by the mere presence of motifs. Alternatively, nucleic acid sequences are incorporated into a vector and introduced into a host cell. The gene product encoded by the nucleic acid is expressed and detected. Often, screening is accomplished in vitro (see, for example, DeGraaf et al., Gene, 128 (1), 13–17 (1993)). For instance, nucleic acids from a library are expressed and the peptides are collected and assayed. Yet, in vitro assays are not predictive of in vivo activity, and the data collected is not easily converted into information useful to, for example, the pharmaceutical industry.

Despite the construction of genetic libraries, much of the genome remains a mystery as to the function of encoded gene products. Genomics data does not take into account pre- and post-translational processing of gene products, nor does it give any indication as the amount of peptide produced or whether a peptide is active. Therefore, it would be advantageous and more relevant to study the vast array of proteins within a cell. The term "proteomics" has been used to refer to the large-scale analysis of proteins and functional genomics.

Traditionally, the tool used for proteomics research is two-dimensional polyacrylamide gels. Two-dimensional gel electrophoresis allows the separation of many proteins from a cell lysate based on charge and mass. Proteins separated in this manner can be quantitated, catalogued, and analyzed. However, two-dimensional gels are frequently not reproducible, and the identification of the proteins separated on the gel is not straightforward. In addition, only abundantly produced proteins can be detected, as proteins are difficult to amplify. In addition, some protein complexes, such as membrane protein complexes, are hard to separate. Moreover, two-dimensional gel electrophoresis is time-consuming and labor-intensive.

Like two-dimensional gel electrophoresis, yeast two-hybrid systems also are useful in protein research. Yeast two-hybrid systems are particularly useful in determining protein-protein interactions. However, the yeast two-hybrid system has been plagued with problems with false-negative and false-positive results and usually takes months to develop even preliminary results.

Similarly, phage display libraries are used to express and screen proteins for binding to a target molecule. In phage display libraries, peptides of interest are expressed in the phage coat and displayed to the environment. Phage display libraries have been used to screen proteins in vitro by association of the expressed peptide with a target ligand. However, the utility of phage display libraries to associate function with a genetic sequence in vitro is limited in that few targets have been identified, much less successfully expressed in their native conformation. Phage display libraries also have been utilized to identify peptides in vivo (see, for example, U.S. Pat. No. 5,622,699 (Ruoslahti et al.)) Yet, gene products identified by function in the context of phage may not necessarily have similar function or activity in other contexts or environments. For example, phage have limited utility in screening in vitro and in vivo for ligands that are efficiently internalized within a cell.

Protein arrays, similar to the DNA arrays commonly used in genomics research, are currently available for the study of protein interactions. Proteins are spotted on a metal chip, which can be exposed to cell lysates, plasma, or targets from pharmaceutical companies, to identify protein interactions. Yet, the fixation of proteins on a surface can cause unfolding of the protein and changes in active site conformations. In addition, the assays must take place in vitro. Thus, the results observed using a chip assay are not necessarily indicative of interactions that occur in vivo.

Accordingly, there remains a need to provide a method of screening genetic libraries. In particular, there remains a need in the art for a method of screening the products of nucleic acid sequences of a genetic library in their natural environment, e.g., intracellularly, to identify a gene product of interest. The present invention provides a rapid, reliable, low-cost method for observing gene product interactions and, advantageously, for characterizing or identifying the encoded gene product. These and other advantages of the present invention, as well as additional inventive features, will be apparent from the description of the invention provided herein.

BRIEF SUMMARY OF THE INVENTION

The present invention provides a method of identifying a gene product. The method comprises providing a multiplicity of cells comprising a first gene product. A library of second nucleic acid sequences encoding second gene products is introduced into the multiplicity of cells. The second nucleic acid sequences are expressed in the multiplicity of cells to produce the second gene products such that the first gene product and at least one of the second gene products contact. Preferably, the first gene product and at least one of the second gene products contact intracellularly. The method further comprises causing a complex to form between the first gene product, an affinity molecule, and at least one of the second gene products, and subsequently retrieving the complex. At least one second gene product of the complex then is identified. Preferably, the first gene product is produced in the multiplicity of cells via expression of a first exogenous nucleic acid sequence encoding the first gene product.

The present inventive method further provides a method of identifying a gene product comprising providing a viral vector comprising a first nucleic acid sequence encoding a first gene product and providing a library of viral vectors. Each member of the library of viral vectors comprises a second nucleic acid sequence encoding a second gene product. The method further comprises transducing a multiplicity of host cells with the viral vector comprising the first nucleic acid sequence and the library of viral vectors comprising second nucleic acid sequences. The host cells are permissive for expression of the first and second nucleic acid sequences and production of the first and second gene products. The first nucleic acid sequence and second nucleic acid sequences are expressed such that the first gene product and the second gene products contact. Preferably, the first gene product and at least one of the second gene products contact intracellularly. At least one complex is then caused to form between the first gene product, an affinity molecule, and at least one of the second gene products. The formed complex is retrieved, and at least one second gene product of the complex is identified.

DETAILED DESCRIPTION OF THE INVENTION

The present invention provides a method of identifying a gene product. The method comprises providing a multiplicity of cells comprising a first gene product. Preferably, the first gene product is produced in the multiplicity of cells via expression of a first exogenous nucleic acid sequence encoding the first gene product. A library of second nucleic acid sequences encoding second gene products is introduced into the multiplicity of cells. The method further comprises expressing the second nucleic acid sequences to produce the second gene products such that the first gene product and at least one of the second gene products contact. Preferably, the first gene product and at least one of the second gene products contact intracellularly. At least one complex is caused to form between the first gene product, an affinity molecule, and at least one of the second gene products. The method further comprises retrieving the complex and identifying at least one second gene product of the complex. The present inventive method can be utilized to isolate and/or identify a gene product of interest based on binding to another gene product, as well as characterize gene product interactions.

In the present inventive method, a multiplicity of cells is provided which comprises a first gene product. The first gene product can be introduced into the multiplicity of cells using any suitable method. For example, the first gene product can comprise a signal sequence that allows passage of the first gene product through the host cell membrane. Desirably, the first gene product is produced in the multiplicity of cells via expression of a first exogenous nucleic acid sequence encoding the first gene product. Preferably, the cells are permissive for expression of the first and second nucleic acid sequences and facilitate the production of the first and second gene products. The multiplicity of cells can be of any cell type, e.g., prokaryotic or eukaryotic, although eukaryotic cells are preferred. Desirably, the multiplicity of cells is the native environment for the first and/or the second gene product. For example, if one of the gene products encodes an enzyme active in the liver, preferably the multiplicity of cells is derived from hepatocytes. The transduced multiplicity of cells can be cultured in vitro or can be part of, e.g., in a tissue of, a living organism, particularly a plant or animal, preferably a mammal.

The first exogenous nucleic acid sequence and second nucleic acid sequences can be part of any suitable entity that comprises a nucleic acid (i.e., RNA or DNA) that encodes an RNA, protein, or a polypeptide and which is capable of insertion into a multiplicity of cells. Examples of suitable nucleic acid sequences include (1) a DNA consisting, or consisting essentially, of a promoter and an RNA coding region, (2) plasmids, including linear, circular, and supercoiled plasmids, (3) cosmids, and (4) viral gene transfer vectors. Examples of suitable gene transfer vectors comprising RNA include (1) unencapsidated viral RNA, (2) heteronuclear RNA, (3) messenger RNA, and (4) viral RNA that is encapsidated by one or more coat proteins. The nucleic acid sequence optionally can be associated with a liposome, cationic lipids, calcium ions, lithium ions, an antigen binding protein, or any other agent that facilitates the transfer of nucleic acids into a cell. By "exogenous" is meant that the nucleic acid sequence (a) is not native to the host cell or (b) is native to the host cell but is located in a non-native position. For example, an exogenous nucleic acid sequence can be native to a particular host cell, but is expressed from a gene transfer vector, such as a viral vector.

Preferably, the nucleic acid sequence is present in a viral vector. A viral vector useful in the context of the present invention can be any viral vector that mediates insertion of the nucleic acid sequence into a multiplicity of cells. Viral vectors can comprise single-stranded ribonucleic acid (RNA), double-stranded RNA, single-stranded deoxyribonucleic acid (DNA), or double-stranded DNA. Examples of suitable viral vectors include, but are not limited to, viral vectors derived, at least in part, from adeno-associated virus (AAV)-based vectors, retroviral vectors, herpes simplex virus (HSV)-based vectors, AAV-adenoviral chimeric vectors, and adenovirus-based vectors. Any of these expression vectors can be prepared using standard recombinant DNA techniques described in, e.g., Sambrook et al., *Molecular Cloning, a Laboratory Manual*, 2d edition, Cold Spring Harbor Press, Cold Spring Harbor, N.Y. (1989), and Ausubel et al., *Current Protocols in Molecular Biology*, Greene Publishing Associates and John Wiley & Sons, New York, N.Y. (1994). The first nucleic acid sequence and at least one second nucleic acid sequence of the library of second nucleic acid sequences can be present in the same viral vector. The use of viral vectors comprising the first nucleic acid sequence or second nucleic acid sequences solves a problem associated with current proteomics techniques. Previously, only abundantly produced proteins were analyzed in that scarce proteins were not detectable. However, the use of viral vectors, in particular adenoviral vectors, enables the researcher to produce sufficient quantities of previously limited gene products for analysis.

In a preferred embodiment, the first exogenous nucleic acid sequence is present in an adenoviral vector. Also desirably, the second nucleic acid sequences making up the library of second nucleic acid sequences are part of an adenoviral vector, thereby generating a library of adenoviral vectors. Adenovirus is easy to use, can be produced in high titers (i.e., up to about $10^{13}$ viral particles/ml), and transfers genes efficiently to nonreplicating, as well as replicating cells (see, for example, review by Crystal, *Science*, 270, 404–410 (1995)). Adenoviral vectors exhibit a broad range of host- and cell-type specificity and, if desired, can be manipulated to target a specific cell type. Therefore, it is possible to identify a gene product based upon gene product interactions specific to a cell type or tissue, which is advantageous in instances where interaction of the first gene product and the second gene product is dependent on cell-specific post-translational modifications. In addition, adenoviral vectors can be manipulated to accept large DNA molecules up to about 36 kb. The characterization of the interaction between gene products or the identity of a gene product can be determined in the context of its natural intracellular or cell surface environment in vivo using adenovirus to express the gene product(s). It will be appreciated that identifying eukaryotic gene products and determining eukaryotic protein-protein interactions in eukaryotic cells is more accurate than other methods wherein eukaryotic gene products are screened in bacterial cells or in soluble form in vitro.

Indeed, the use of viral vectors, in particular adenoviral vectors, enables the identification of a second gene product that interacts with a first gene product and characterization of the gene product interactions in vivo. An entire library of second nucleic acid sequences or a subset of the library can be administered to an animal or introduced into host cells in vitro or in vivo. Alternatively, the sublibrary comprising a population of identical second nucleic acid sequences, a library comprising a complexity of 1, can be introduced into an individual animal. The library of second nucleic acid sequences can be administered to a healthy animal, a diseased animal, or a transgenic animal in order to screen the library in a particular in vivo environment.

In the context of the present invention, the adenoviral vector can be derived from any serotype of adenovirus. Adenoviral stocks that can be employed as a source of adenovirus can be amplified from the adenoviral serotypes 1 through 51, which are currently available from the American Type Culture Collection (ATCC, Manassis, Va.), or from any other serotype of adenovirus available from any other source. Preferably, the adenoviral vector is derived from adenovirus serotypes 2 or 5. Preferred methods of constructing and/or purifying adenoviral vectors are set forth in, for example, U.S. Pat. No. 5,965,358 and International Patent Applications WO 98/56937, WO 99/15686, and WO 99/54441.

The adenoviral vector is preferably deficient in at least one gene function required for viral replication, thereby resulting in a "replication-deficient" adenoviral vector. Preferably, the adenoviral vector is deficient in at least one essential gene function of the E1 region, e.g., the E1a region and/or the E1b region, of the adenoviral genome. In addition to a deficiency in the E1 region, the recombinant adenovirus also can have a mutation in the major late promoter (MLP), as discussed in International Patent Application WO 00/00628. More preferably, the vector is deficient in at least one essential gene function of the E1 region and at least part of the E3 region (e.g., an Xba I deletion of the E3 region). Preferably, the adenoviral vector is "multiply deficient," meaning that the adenoviral vector is deficient in one or more essential gene functions required for viral replication in each of two or more regions. For example, the aforementioned E1-deficient or E1-, E3-deficient adenoviral vectors can be further deficient in at least one essential gene of the E4 region and/or at least one essential gene of the E2 region (e.g., the E2A region). Adenoviral vectors deleted of the entire E4 region can elicit lower host immune responses. Alternatively, the adenoviral vector can lack all adenoviral sequences except the inverted terminal repeats (ITRs) and packaging signal or ITRs and at least one adenoviral promoter, thereby forming an adenoviral amplicon. Suitable replication-deficient adenoviral vectors are disclosed in U.S. Pat. Nos. 5,851,806 and 5,994,106 and International Patent Applications WO 95/34671 and WO 97/21826.

Similarly, the coat protein of a viral vector, preferably an adenoviral vector, can be manipulated to alter the binding specificity or recognition of a virus for a viral receptor on a potential host cell or to aid the vector in evading the immune system. For adenovirus, such manipulations can include deletion of regions of the fiber, penton, or hexon, insertions of various native or non-native ligands into portions of the coat protein, and the like. Manipulation of the coat protein can broaden the range of cells infected by a viral vector or enable targeting of a viral vector to a specific cell type. One direct result of this increased efficiency of entry is that the virus, preferably, the adenovirus, can bind to and enter numerous cell types which a virus comprising wild-type coat protein typically cannot enter or can enter with only a low efficiency. Alternatively, a chimeric virus coat protein not selective for a specific type of eukaryotic cell can be generated. In this embodiment, the chimeric virus coat protein efficiently binds to a broader range of eukaryotic cells than a wild-type virus coat, such as described in International Patent Application WO 97/20051. Suitable modifications to a viral vector, specifically an adenoviral vector, including modifications to coat proteins, are described in U.S. Pat. Nos. 5,559,099; 5,731,190; 5,712,136; 5,770,442; 5,846,782; 5,926,311; 5,965,541; 6,057,155; 6,127,525; 6,153,435 and International Patent Applications WO 96/07734, WO 96/26281, WO 97/20051, WO 98/07865, WO 98/07877, WO 98/54346, and WO 00/15823.

By "library of second nucleic acid sequences" is meant a collection of nucleic acid molecules, which are the same, i.e., the nucleic acid sequences encode the same peptide or functional nucleic acid sequence or variations thereof, or different, i.e., the nucleic acid sequences encode different peptides or functional nucleic acid sequences. By "functional nucleic acid sequence" is meant a nucleic acid sequence, i.e., DNA or RNA, that performs a function or has an activity within a cell. An example of a functional nucleic acid is antisense RNA that impedes transcription or translation of a DNA or RNA sequence. The library of second nucleic acid sequences can be obtained from any source. For example, the second nucleic acid sequences can be genomic DNA obtained from a source in nature that has not been genetically modified. The library of second nucleic acid sequences also can be obtained from an organism that has been modified to exhibit a particular phenotype. The second nucleic acid sequences can comprise cDNA or can be synthetically made using routine methods known in the art. If required, the second nucleic acid sequences can comprise pieces of larger molecules of DNA fragmented by chemical, enzymatic, or mechanical means. The library of second nucleic acid sequences also can comprise polymerase chain reaction (PCR) products of DNA segments, and the like. Preferably, the second nucleic acid sequences are obtained from a population of DNA comprising a multiplicity of genetic elements.

The probability of identifying a gene product with a desired activity depends greatly on the diversity of the genetic library. It is, therefore, advantageous to mutate the DNA fragments to obtain optimal diversity in the library of second nucleic acid sequences. Nucleic acid sequences can be mutated using numerous methods well understood in the art, such as, for example, exposure to mutating chemical agents, e.g., ethidium bromide, recursive shuffling (see, for example, International Patent Application WO 98/13485), error-prone PCR, error-prone transcription, and the like. However, mutation of the second nucleic acid sequences is not required. When screening genomic libraries to associate a function with a nucleotide sequence, for example, the second nucleic acid sequences are preferably not mutated.

The exogenous first nucleic acid sequence and the library of second nucleic acid sequences can be introduced or inserted into the multiplicity of host cells by any suitable method. Suitable methods comprise infection (e.g., mediated by a coat-protein), precipitation and co-incubation of the vector with suitable salts (e.g., $CaCl_2$ or LiCl), electroporation, particle bombardment, needle-mediated direct injection, transduction, and any other suitable methods for introducing nucleic acids into host cells.

The first nucleic acid sequence and/or the second nucleic acid sequences can be constitutively expressed at a suitable level, can be repressible, and/or can be induced in response to a stimulus initiated from inside or outside the transduced host cells. If the nucleic acid sequence requires transcription, any suitable promoter can be used to drive the transcription of the nucleic acid sequence. Suitable promoters comprise both viral and cellular promoters. Suitable viral promoters are known in the art and include, for instance, cytomegalovirus (CMV) promoters, such as the CMV immediate-early promoter, promoters derived from human immunodeficiency virus (HIV), such as the HIV long terminal repeat promoter, Rous sarcoma virus (RSV) promoters, such as the RSV long terminal repeat, mouse mammary tumor virus (MMTV) promoters, HSV promoters, such as the herpes thymidine kinase promoter (Wagner et al., *Proc. Natl. Acad. Sci.* (*USA*), 78, 144–145 (1981)), promoters derived from SV40 or Epstein Barr virus, and the like. Preferably, the viral promoter is an adenoviral promoter, such as the Ad2 or Ad5 major late promoter and tripartite leader, a CMV promoter, or an RSV promoter. Other suitable promoters for use in the methods of the present invention include the regulatory sequences of the metallothionine gene (Brinster et al., *Nature*, 296, 39–42 (1982)), promoter elements from yeast or other fungi such as the Gal 4 promoter, the alcohol dehydrogenase promoter, the phosphoglycerol kinase promoter, and the alkaline phosphatase promoter. Similarly, promoters isolated from the genome of mammalian cells, such as the □-actin promoter or the muscle-creatine promoter, can be employed. Induction or de-repression of transcription, where appropriate, can be regulated by any suitable condition inside the cell (such as, for example, adenosine diphosphate concentration, stage of the cell cycle, and isoforms of p53 present) or by any suitable external stimulus (such as, for example, hypoxia, provision of metal ions to the cell, elevation of cellular temperature, provision of a small signaling molecule, e.g., a steroid, saccharide, or lipid, or exposure to non-background radiation).

In certain embodiments, it can be advantageous to modulate expression of the first and/or second nucleic acid sequences. A suitable method of modulating expression of a nucleic acid sequence comprises addition of site-specific recombination sites to the expression vector. Contacting an expression vector comprising site-specific recombination sites with a recombinase will either up- or down-regulate transcription of a coding sequence, or simultaneously up-regulate transcription one coding sequence and down-regulate transcription of another, through the recombination event. Use of site-specific recombination to modulate transcription of a nucleic acid sequence is described, for example, U.S. Pat. Nos. 5,801,030 and 6,063,627 and International Patent Application WO 97/09439.

The first gene product and/or the second gene product(s) are preferably RNA transcripts or a translated proteins, but also can be post-transcriptional or post-translation products encoded by the exogenous nucleic acid sequence and modified by enzymes or chemical moieties in the cytosol, extracellular medium, or in a reaction vessel. An advantage of the present inventive method is that gene products to be screened can be modified intracellularly so as to obtain a more accurate picture of the function of the encoded gene products in vivo. The second nucleic acid sequences are expressed to produce the second gene products such that the first gene product and at least one of the second gene products contact (i.e., the second gene product(s) and the first gene product are expressed under conditions wherein the second gene product(s) and first gene product contact and, if appropriate, associate or bind. Preferably, the first gene product and at least one of the second gene products contact intracellularly. However, the first gene product and/or at least one of the second gene products can be secreted gene products, e.g., a secreted growth factor. Therefore, it is also appropriate that the first gene product and at least one of the second gene products contact extracellularly. Desirably, the gene products directly or indirectly associate and form a complex comprising the first gene product and at least one second gene product. The association can be through any suitable manner, e.g., a covalent bond, a non-covalent bond, or both. Preferably, the bond is stable and strong enough to allow for one or more washing or isolation steps without causing or allowing the termination of the association between the first and second gene products. The present inventive method is superior to previously described proteomics methods in that the first gene product and the second gene products interact in the presence of intracellular molecules that can interfere with recognition and binding. In other words, preferably the gene products are allowed to contact prior to purifying the gene products in order to achieve a more accurate interaction than achieved with previous techniques. Previous methods of screening a library in vitro cannot adequately mimic intracellular conditions, unlike the method of the present invention.

The present inventive method further comprises causing at least one complex to form between the first gene product, an affinity molecule, and at least one of the second gene products, and retrieving the formed complex. In the context of the present invention, an affinity molecule is a molecule that associates with the first gene product and can be used to at least partially separate the first gene product (and molecules associated therewith) from other molecules that do not associate with the first gene product. The contacting of the first gene product with the affinity molecule causes a complex to form between the affinity molecule, the first gene product, and one or more second gene products. Although forming an association between the first gene product and an affinity molecule aids in isolation of the complex of the first gene product and the second gene product(s), use of an affinity molecule is not necessary so long as the complex can be retrieved by other means. Exemplary of suitable affinity molecules are antibodies or antigenically-reactive fragments thereof, metal ions (e.g., zinc, cobalt, nickel, or copper), which are bound with high-affinity by polyhistidine, as well as other DNAs, RNAs, and proteins used in the art to separate molecules. Antibodies to the first gene product can be generated using routine immunology methods. Alternatively, the first gene product can comprise a heterologous portion that associates with an affinity molecule. Suitable heterologous portions, or tags, include the FLAG epitope, the hemagluttenin (HA) epitope, or other antigenic epitopes recognized by an antibody and that can be fused to the first gene product.

Complexing the gene products with an affinity molecule allows the partial or total separation of the first gene product along with any associated second gene products, from other molecules which can contact the gene products, such as those in the cell, cell lysate, or (especially in the case of secreted proteins) the cellular medium. The complex can be partially isolated and retrieved by taking advantage of any suitable property of the affinity molecule or the complex comprising the affinity molecule. To facilitate retrieval of the complexes, preferably the affinity molecule is fixed to (e.g., adhered to or forms part of) a solid support, such as a bead or affinity column. The complex can be separated, for instance, by affinity chromatography (such as protein A or gel Blue A chromatography), molecular sieving chromatography, selective adherence to a solid substrate, or selective precipitation. Preferably, the complex is partially isolated by selective precipitation or selective adherence to a derivatized mass spectrometry slide.

Once the complex is retrieved, the second gene product can be identified. Desirably, the complex between the first gene product, the affinity molecule, and at least one of the second gene products is dissociated such that the first gene product and at least one second gene product remain intact. In other words, in identifying the second gene product, preferably the affinity molecule is removed from the complex. By keeping the binding pair intact, the molecular weight of the associated gene products can be determined. Alternatively, the complex can be completely dissociated such that the affinity molecule, the first gene product, and at least one second gene product are separated, although this is less desired in some embodiments. At least one second gene product then can be identified using a variety of techniques. For example, the second gene product can be sequenced using, for example, Edman degradation and subsequently compared to amino acid sequences listed in various computer databases. If desired, the second nucleic acid sequence (i.e., the nucleic acid encoding the second gene product) can be identified.

Alternatively, the second gene product can be identified based on physical properties. In one embodiment, identifying at least one second gene product of the complex comprises producing charged fragments from at least a portion of the complex. In this aspect, the present inventive method is superior to other methods in proteomics in that separation of the first gene product and second gene product(s) is not required. It is, of course, preferable to avoid additional steps (e.g., selective precipitation, liquid chromatography (other than desalting), gel electrophoresis, and differential centrifugation) because these steps increase the complexity of the method and increase time and cost requirements. The charged fragments are detected by a detector which produces a signal corresponding to the mass-to-charge ratio of the charged fragments. Optionally, the complex can be isolated and disassociated into its component molecules prior to charging and fragmenting, although this is less preferred in some embodiments. Additionally, individual molecular components of the complex can be re-isolated from the disassociated complex before producing charged fragments such that the resulting sample signal will be significantly simplified. The signal comprises information characteristic of at least the second gene product and, optionally, the first gene product and/or affinity molecule. The produced signal is then evaluated to identify the second gene product. Optionally, the signal comprising information characteristic of the second gene product is compared to a standard signal generated from the first gene product alone or a complex of the first gene product and the affinity molecule.

The generated signal desirably comprises a fingerprint that allows the identification of the second gene product, or at least its sequence. If the complex is not dissociated, at least one second gene product can be detected by the presence of data in the signal that does not reflect mass-to-charge values corresponding to charged fragments of the first gene transfer vector product or the affinity molecule. Any suitable technique can be used to characterize the second gene product once it is detected. For example, the second gene product can be characterized by comparison with a standard signal, or by other techniques such as, but not limited to, subjecting the second gene product to chromatography, differential gradient analysis (e.g., a cesium chloride gradient column or sucrose gradient), electrophoresis, centrifugation, ELISA, or any combination of the aforementioned or other techniques.

In one particular aspect of the invention, the characterization of at least one detected second gene product can be achieved by subjecting one or more charged fragments of the second gene product to further fragmentation and analysis. In this particular aspect, secondary charged fragments are produced from a charged fragment(s) generated from the second gene product. The secondary charged fragments then can be detected by a detector that produces a signal corresponding to the mass-to-charge ratio of the detected secondary second gene product fragment. This signal (e.g., a spectrum) corresponding to the mass-to-charge ratio of the secondary second gene product charged fragments allows for rapid identification of the second gene product.

Any suitable technique or combination of techniques can be used to produce charged fragments from at least one second gene product, detect the charged gene product fragments, and generate a signal corresponding to the mass-to-charge ratio of the charged second gene product fragments. The gene products are charged (e.g., a proton is added to an electrically neutral gene product without cleaving the gene product) and, preferably, charged and fragmented. The charged fragments can be produced by any suitable technique, for example, a technique comprising contacting at least one retrieved second gene product with light, energy, or a chemical. Preferably, the charged fragments will be produced by contacting at least one second gene product with radiation, electrons, or protons, and more preferably with protons. Any suitable form of radiation, electrons, or protons can be used in the present inventive method to produce charged fragments from the second gene product. "Radiation" in the context of the present invention refers to any emission of energy in the form of electromagnetic waves, acoustic waves, or particles. Examples of radiation suitable in the context of the present invention include, but are not limited to, radio waves, microwaves, visible light, ultraviolet (UV) light, far UV and infrared rays, x-rays, gamma-rays, infrasonic waves, sonic waves, ultrasonic waves, and $\alpha$- and $\beta$-rays of radioactivity. The electrons can be in any suitable form. For example, the electrons can be in the form of electron beams or individual electrons. Similarly, the protons can be in any suitable formn. Moreover, the radiation, electrons, and protons can be from any suitable source. For example, radiation can be emitted from a natural source (e.g., radioactive cobalt), an x-ray device, or a laser. Preferably, the charged fragment of the second gene product is further fragmented, for example, by collision-induced dissociation (CID), to produce the secondary charged fragments of at least one second gene product.

The radiation, electrons, and protons can have any suitable characteristics. In particular, the radiation can have any suitable wavelength, for example, in the infrared spectrum of the ultraviolet spectrum. Similarly, any pulse width suitable to produce charged fragments can be utilized in the present inventive method. For example, the pulse generated by a laser can have a width of from about 1 to about 10 nanoseconds (e.g., 3 nanoseconds) and can have a width up to about 20, 50, 75, 100, 200, or even 5,000 nanoseconds. Moreover, variable pulse widths and multiple repeated pulses can be used to produce the charged fragments.

The charged fragments can be in any state or quantity suitable for fragment detection. For example, a sample comprising the gene transfer vector product can be vaporized at the time the charged fragments are produced, such that the charged fragments enter into a gaseous or vapor state, have greater mobility, and are subject to easier detection. The charged fragments can have any suitable velocity at the time of production that allows fragments to be accelerated, after they are produced, to a desired velocity before the charged fragments are detected. The charged fragments can pass through a field-free region, wherein the velocity of the charged fragments within the field-free region is proportional to the mass-to-charge ratio of the charged fragments. One example of such a field-free region is an electric field, particularly an electric field wherein lighter charged fragments have a higher velocity than heavier charged fragments. While acceleration of charged fragments is not required, if the charged fragments are accelerated, any level of acceleration sufficient for detection of the charged fragments can be used. For example, the charged fragments can be accelerated to a fixed kinetic energy by contacting the charged fragments with an electric potential.

The detection of the charged fragments of at least one second gene product is accomplished by any suitable technique. The detection can include, for example, measuring the time-of-flight of the detected charged fragments, wherein the time-of-flight is the approximate time required for a charged fragment to travel a distance across a field-free region. A signal corresponding to the time-of-flight then can be generated.

While the fragmentation and detection steps of the present inventive method can be performed in any suitable manner, they are preferably performed by the use of an analytical device, most preferably by the use of an ion source and a mass analyzer, such as are present in mass spectrometers. Suitable ion sources comprise electron impact, fast ion or atom bombardment, ion spray, field desorption, laser desorption (including, but not limited to matrix-assisted laser desorption ionization (MALDI)), plasma desorption, thermospray, electrospray ionization (including, but not limited to, nanoelectrospray ionization and/or capillary electrospray), inductively coupled plasma, chemical ionization (including, but not limited to atmospheric pressure chemical ionization (APCI)), and atmospheric pressure ionization (including, but not limited to, APCI). Preferred ion sources comprise MALDI, thermospray, electrospray ionization (ESI), and atmospheric pressure ionization (API).

Suitable mass analyzers comprise quadrupole analyzers (e.g., single-quadrupole or triple quadrupole), ion trap or quistor analyzers, time-of-flight (TOF) analyzers, TOF/TOF analyzers, hybrid quadrupole/time-of-flight mass analyzers, magnetic and electromagnetic analyzers, ion cyclotron resonance analyzers, and Fourier transform mass analyzers. Preferably, the charged fragments are detected by a mass analyzer selected from the group of mass analyzers consisting of a time-of-flight, a single quadrupole, a triple quadrupole, a hybrid quadrupole/time-of-flight, a Fourier transform, an ion trap, a single focusing magnetic deflection instrument, and a double focusing magnetic focusing instrument. Other mass spectrometers that can be used in the context of the present invention comprise an electrospray ionization mass spectrometer, a plasma desorption spectrometer, a thermospray ionization spectrometer, and a laser desorption mass spectrometer.

Most preferably, a MALDI-TOF spectrometer with precursor selector (or "ion gate") capabilities, a quadrapole electrospray spectrometer, or any spectrometer capable of focusing on one or more signals that correspond to at least one second gene product is used to produce, detect, and analyze the originally produced and, where applicable, secondary charged second gene product fragments. A MALDI-TOF spectrometer with precursor selector capabilities is particularly preferred because it is capable of accurately detecting (and focusing) on a signal corresponding to at least one second gene product, isolating the originally-produced second gene product fragment, and rapidly performing further analysis on the isolated second gene product fragment.

Improved resolution and faster analysis can sometimes be obtained using tandem mass spectrometry. Additionally, by using tandem mass spectrometry (e.g., by using a spectrometer possessing two detectors and a reflectron), identification of monoisotopic masses versus average masses is possible.

The charged fragments can have any suitable size for detection, sample signal production, and analysis. For example, the produced and detected charged fragments can have molecular weights of up to 5,000 daltons (i.e., atomic mass units), 30,000 daltons, 150,000 daltons, or even 300,000 daltons or more. Similarly, the charged fragments can have any suitable mass-to-charge ratio for detection, sample signal production and analysis. For example, the produced and detected charged fragments can have mass-to-charge ratios (m/z) of at least 50, 100, 200, 400, 500, 1,000, 2,500, 5,000, 10,000, 20,000, or even 25,000, 300,000 or more.

The sample signal generated upon detection of the charged fragments can be any type of signal that allows for evaluation and, optionally, comparison to a standard signal, and can be generated in any suitable manner. Similarly, a standard signal can be any signal, in any form, that allows for useful comparison with a sample signal to detect, for example, protein-protein interactions. The standard signal can be a single signal or a group (or series) of signals. The sample and standard signals can be associated with any suitable single mass-to-charge ratios. The sample signal and standard signal can be presented in similar or different (though preferably similar) formats, measurements, or units. For example, a suitable standard signal can be a signal that is produced from techniques similar to those that are used to generate the sample signal. More specifically, the standard signal can be a signal that is generated from a standard source, e.g., the first gene product.

An example of this aspect of the invention is the identification of the amino acid composition of a second gene product by the technique described above. After identifying a signal corresponding to at least one second gene product, the second gene product can be further fragmented (e.g., by CID). By controlling fragmentation, charged fragments corresponding to individual constituent amino acids can be produced. Signals corresponding to the amino acids then are generated by a detector, allowing rapid determination of the amino acid composition of the polypeptide.

Any of the individual steps of the present inventive method can be repeated two or more times. For example, the production of charged fragments and the detection of the charged fragments can be repeated two or more times to provide a satisfactory sample signal(s). Methods of producing and detecting charged fragments to produce a signal corresponding to the mass-to-charge ratio of the charged fragments to evaluate genetic materials are further described in U.S. Pat. No. 5,965,358 and International Patent Applications WO 00/12765 and WO 01/11087.

Therefore, in one embodiment of the present invention, the method of identifying a gene product comprises providing a viral vector comprising a first nucleic acid sequence encoding a first gene product and providing a library of viral vectors, wherein each viral vector of the library comprises a second nucleic acid sequence encoding a second gene product. Desirably, the viral vectors are adenoviral vectors. The method further comprises transducing a multiplicity of host cells with the viral vector comprising the first nucleic acid sequence and the library of viral vectors comprising second nucleic acid sequences using any suitable method, e.g., routine methods known in the art. Preferably, the viral vectors are adenoviral vectors, as described herein. The host cells are permissive for expression of the first and second nucleic acid sequences and production of the first and second gene products. The first nucleic acid sequence and the second nucleic acid sequences are then expressed in the multiplicity of host cells such that the first gene product and at least one of the second gene products contact. Preferably, the first gene product and at least one of the second gene products contact intracellularly. Alternatively, the first gene product and/or at least one of the second gene products is secreted from the multiplicity of cells, and the first gene product and at least one of the second gene products contact extracellularly. To aid in identifying at least one second gene product, at least one complex is caused to form between the first gene product, an affinity molecule, and at least one of the second gene products. At least one complex then is retrieved, and at least one second gene product of the complex is identified. Preferably, the first gene product comprises a heterologous portion which associates with the affinity molecule to ensure specific binding of the affinity molecule to the first gene product.

While at least one second gene product can be identified using a variety of methods, preferably identifying at least one second gene product of the complex comprises producing charged fragments from at least a portion of the complex. The charged fragments are detected by a detector which produces a signal corresponding to the mass-to-charge ratio of the charged fragments and comprising information characteristic of the second gene product. The signal is then evaluated to identify the second gene product, as described herein.

A library of viral vectors, e.g., adenoviral vectors, preferably comprises, consists essentially of, or consists of a multiplicity of viral vectors comprising a multiplicity of genetic elements. Any number of individual viral vectors can make up the library of viral vectors. Likewise, any number of second nucleic acid sequences can make up a library of second nucleic acid sequences. The complexity of the library of viral vectors can vary according to the particular embodiment. By "complexity" is meant the number of unique individuals in the library. Preferably, the complexity of the library of viral vectors is about 1 to about $10^{11}$ colony forming units. More preferably, the complexity of the library is about 1 to about $10^6$ colony forming units, or unique individuals. In other words, the complexity of the library viral vectors preferably is 2 (e.g., 3, 5, 10, $10^2$, $10^3$, etc.) to $10^9$ (e.g., 10, $10^2$, $10^3$, $10^4$, $10^5$, $10^6$, $10^7$, $10^8$, or any other integer within the range of 2 to $10^9$) particles.

The present inventive method can be performed multiple times in order to identify or isolate a gene product. For example, the present inventive method can be performed at least 2, 3, 4, or more times (e.g., at least 5, 7, 10, 15, or 20 times) in order to identify a gene product of interest. Moreover, the identified gene products can be re-entered into the present inventive method to identify additional gene products. In other words, a previously identified -second gene product can be used in subsequent rounds of screening as the "first gene product" in order to identify gene products that interact with that previously identified second gene product. Using the identified gene products in this manner, and repeating the process any number of times as described above, entire cellular pathways can be mapped.

The binding of at least one of the second gene products to the first gene product can be verified or evaluated by exposing the first gene product and at least one second gene product to an entity which specifically inhibits association of the first and second gene products (e.g., a binding inhibitor). For example, the first gene product and at least one of the second gene products are peptides, and the second gene product(s) is identified. To confirm the identity of the second gene product(s) or to evaluate the peptide-peptide interactions between the first and second gene products, the first gene product and the identified second gene product(s) are allowed to contact in the presence of, for example, a small molecule or biomolecule known to interfere with binding. The peptide-peptide interaction can be evaluated, for instance, to confirm that the second peptide specifically binds the first peptide. In addition, the affinity of the second gene product for the first gene product can be characterized. For example, if using mass spectroscopy, the relative intensity of the peaks of the spectra corresponding to the binding pair can be used to evaluate the affinity of the binding partners.

In this regard, the techniques described herein can be used to evaluate peptide-peptide interactions, as well as identifying gene products. For instance, once interacting gene products are identified, the system described herein can be used to identify targets, i.e., small molecules, that inhibit, disrupt, augment, or do not impact the peptide-peptide interaction. In this aspect, the first peptide and the second peptide are allowed to contact in the presence of a potential target, e.g., a small molecule, compound, or biomolecule that enhances, inhibits, or has no effect on binding of the first and second peptides. Any peptide-peptide interactions are evaluated by any suitable method. Peptide-peptide interactions are preferably evaluated by producing charged fragments from at least a portion of the complex, detecting the charged fragments using a detector that produces a signal corresponding to the mass-to-charge ratio, and evaluating the signal to evaluate the peptide-peptide interaction. The signal generated from the peptide-peptide complex that formed in the presence of the target is compared to a standard signal generated from a peptide-peptide complex formed without the target. Comparison of the signals provides information regarding the inhibitory or enhancing effect of the target on peptide-peptide binding. Any of the methods described herein can be repeated any number of times to screen a library of potential targets, such as those generated in pharmaceutical research. The second gene product used to screen target molecules as described above can be produced by expressing a second nucleic acid sequence selected from a library comprising a complexity of one.

The present inventive method also can be utilized to construct personal, patient-specific therapeutics. It is apparent in the clinic that potential therapeutics do not act similarly in all patients. It is, therefore, desirable to create therapeutic agents and treatment regimens tailored for individual patients. To determine the efficacy of a potential therapeutic, a library of second nucleic acid sequences can be constructed from genomic DNA from an individual patient, tissue, or organ. A first nucleic acid sequence is provided that encodes the potential therapeutic agent. The first nucleic acid sequence and the second nucleic acid sequence(s) are expressed under conditions wherein the first gene product and at least one second gene product interact to form a complex. Formation of a complex is indicative of an interaction of the therapeutic agent with a cellular factor encoded by the second nucleic acid sequence and, therefore, provides valuable information to a clinician as to the likelihood that a candidate biotherapeutic would affect a biological response. Moreover, the second gene product can be identified to determine what cellular factor associates with the potential therapeutic. Alternatively, instead of constructing a genetic library from a patient's cells, a population of cells (such as cells isolated from a biopsy) can be lysed to provide a library of cellular factors into which is introduced the potential therapeutic in vitro. Also alternatively, a population of cells (e.g., a library of cells) is infected with adenoviral vectors comprising the first nucleic acid sequence. Any complexes formed by the therapeutic and the cellular factor(s) are isolated and the cellular factor identified using, for example, mass spectroscopy, as described herein. Using the techniques described herein, relevant protein-protein and protein-therapeutic interactions in specific tissues can be elucidated.

In addition, the data generated from the techniques described herein, including data concerning the identification of the gene products, the interaction of gene products, and the screening of target molecules which do or do not affect the interaction of gene products, can be compiled, organized, screened, and/or sorted in any fashion. For example, the data generated using any of the techniques described herein can be compiled into a database, e.g., a database accessible via the internet, to provide access to the gathered information in a meaningful format.

The following example further illustrates the present invention but, of course, should not be construed as in any way limiting its scope.

EXAMPLE

This example illustrates the association of a first gene product, the identity of which is known in advance, with a second gene product, and the subsequent detection of the second gene product.

A cDNA ("a first exogenous nucleic acid sequence") encoding a chimeric fusion protein of the 14.7K gene product and a heterologous region encoding a polypeptide that associates with high affinity to antibodies specific for hemagluttenin (HA) ("a first gene product"), and separately a cDNA ("a second nucleic acid sequence") encoding the gene product of the adenoviral-E3 14.7K gene ("a second gene product"), were subcloned by standard techniques into a DNA to form expression cassettes that were transcriptionally regulated by a CMV immediate-early promoter and an SV40 early polyadenylation signal. Each of these two expression cassettes was inserted into the deleted E1 region of separate E1-, E3-deleted adenoviral gene transfer vectors. The resulting adenoviral gene transfer vectors were named Ad14.7HA and Ad14.7, respectively. A stock of each adenoviral gene transfer vector was produced by standard techniques.

HEK-293 cells were co-infected with a sample of each of the Ad14.7HA stock and the Ad14.7 stock. About 17 hours later (i.e., after infection), the 293 cells were lysed with detergents, and the insoluble fraction was removed by low-speed centrifugation. A monoclonal anti-HA antibody ("an affinity molecule") bound by Protein A-sepharose beads (PAS-beads, Boehringer Mannheim) then was added to the soluble fraction of the cell lysate. The mixture was incubated with rocking at 4° C. overnight.

A complex comprising the 14.7K-HA protein, the 14.7K protein, the monoclonal antibody, and the PAS-beads (i.e., a complex of the first gene product, the affinity molecule, and the second gene product) formed, which complex was separated from the soluble fraction of the lysate by centrifugation. The complex was washed three times with phosphate buffered saline. The complex was suspended in 1% trifluoroacetic acid (TFA), which caused the complex to disassociate. The PAS-beads, which are insoluble, were allowed to settle, and the supernatant fraction was transferred to a new container.

The supernatant fraction, in which proteins from the complex were suspended, was dried and resuspended in 0.1% TFA, and applied to a ZipTip C18 (Millipore) desalting column to reduce the concentration of salts, detergents, and any other small molecules which may have been associated with the complex. The proteins were eluted from the ZipTip C18 desalting-column with a mixture containing 50% acetonitrile, 0.1% TFA, and 10 mg/ml sinapinic acid.

Charged fragments of the eluted material were produced, and the mass-to-charge ratios of the charged fragments were detected with a MALDI-TOF mass spectrometer (PE BIO Systems). The sample signal produced by the mass spectrometer comprised peaks with mass-to-charge ratios equivalent to the predicted mass of the 14.7 and 14.7HA proteins. Evaluation of the sample signal indicated that the adenoviral E3-14.7K protein (i.e., the second gene product) associates with a chimeric fusion protein comprising the E3-14.7K protein and an HA-epitope (i.e., the first gene product).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of identifying a gene product, wherein the method comprises:
   (a) providing a multiplicity of cells comprising a first gene product;
   (b) introducing into the multiplicity of cells a library of second nucleic acid sequences encoding second gene products;
   (c) expressing the second nucleic acid sequences to produce the second gene products such that the first gene product and at least one of the second gene products are secreted from the multiplicity of cells, and the first gene product and at least one of the second gene products contact extracellularly;
   (d) causing at least one complex to form between the first gene product, an affinity molecule, and at least one of the second gene products;
   (e) retrieving the complex; and
   (f) identifying at least one second gene product of the complex, wherein identifying at least one second gene product of the complex comprises:
      (f1) producing charged fragments from at least a portion of the complex;
      (f2) detecting the charged fragments by a detector which produces a signal corresponding to the mass-to-charge ratio of the charged fragments and comprises information about the amino acid sequence of at least one second gene product; and
      (f3) evaluating the signal to identify the at least one of the second gene products.

2. The method of claim 1, wherein the first gene product is produced in the multiplicity of cells via expression of a first exogenous nucleic acid sequence encoding the first gene product.

3. The method of claim 2, wherein the first nucleic acid sequence is present in a plasmid.

4. The method of claim 2, wherein the first nucleic acid sequence is present in a viral vector.

5. The method of claim 4, wherein the viral vector is an adenoviral vector.

6. The method of claim 2, wherein the second nucleic acid sequence is present in a plasmid.

7. The method of claim 2, wherein the second nucleic acid sequence is present in a viral vector.

8. The method of claim 7, wherein the viral vector is an adenoviral vector.

9. The method of claim 1, wherein identifying at least one second gene product of the complex comprises dissociating the complex between the first gene product, the affinity molecule, and at least one of the second gene products such that the first gene product and at least one of the second gene products remain intact.

10. The method of claim 1, wherein the affinity molecule is fixed to a solid support.

11. The method of claim 10, wherein the solid support is a bead or an affinity column.

12. The method of claim 10, wherein identifying at least one second gene product of the complex comprises dissociating the complex between the first gene product, the affinity molecule, and at least one of the second gene products such that the first gene product and at least one of the second gene products remain intact.

13. The method of claim 1, further comprising (g) identifying the second nucleic acid sequence encoding at least one of the second gene products.

14. The method of claim 1, wherein the first gene product comprises a heterologous portion which associates with an affinity molecule.

15. A method of identifying a gene product, wherein the method comprises:
   (a) providing a viral vector comprising a first nucleic acid sequence encoding a first gene product;
   (b) providing a library of viral vectors, wherein each viral vector of the library comprises a second nucleic acid sequence encoding a second gene product;
   (c) transducing a multiplicity of host cells with the viral vector comprising the first nucleic acid sequence and the library of viral vectors comprising second nucleic acid sequences, wherein the host cells are permissive for expression of the first nucleic acid sequence and the second nucleic acid sequences and production of the first gene product and the second gene products;
   (d) expressing the first nucleic acid sequence and the second nucleic acid sequences such that the first gene product and at least one of the second gene products are secreted from the multiplicity of cells, and the first gene product and at least one of the second gene products contact extracellularly;
   (e) causing at least one complex to form between the first gene product, an affinity molecule, and at least one of the second gene products;
   (f) retrieving the formed complex; and
   (g) identifying at least one second gene product of the complex.

16. The method of claim 15, wherein the first gene product comprises a heterologous portion which associates with an affinity molecule.

17. The method of claim 15, wherein the viral vectors are adenoviral vectors.

18. The method of claim 15, wherein identifying at least one second gene product of the complex comprises:
   (g1) producing charged fragments from at least a portion of the complex;
   (g2) detecting the charged fragments by a detector which produces a signal corresponding to the mass-to-charge ratio of the charged fragments and comprising information about the amino acid sequence of at least one of the second gene products; and
   (g3) evaluating the signal to identify at least one of the second gene products.

* * * * *